(12) United States Patent
Hively

(10) Patent No.: US 7,139,677 B2
(45) Date of Patent: Nov. 21, 2006

(54) METHODS FOR CONSISTENT FOREWARNING OF CRITICAL EVENTS ACROSS MULTIPLE DATA CHANNELS

(75) Inventor: Lee M. Hively, Philadelphia, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 880 days.

(21) Appl. No.: 10/195,626

(22) Filed: Jul. 12, 2002

(65) Prior Publication Data

US 2004/0087835 A1 May 6, 2004

(51) Int. Cl.
*G06F 7/02* (2006.01)
(52) U.S. Cl. .................. 702/183; 702/182; 702/19; 600/544; 600/545
(58) Field of Classification Search ............... 600/300, 600/544, 545, 547; 702/19, 22, 182
See application file for complete search history.

(56) References Cited

U.S. PATENT DOCUMENTS

| | | | |
|---|---|---|---|
| 5,626,145 A | 5/1997 | Clapp et al. | |
| 5,743,860 A | 4/1998 | Hively et al. | |
| 5,815,413 A * | 9/1998 | Hively et al. | 702/191 |
| 5,857,978 A * | 1/1999 | Hively et al. | 600/544 |
| 6,484,132 B1 * | 11/2002 | Hively et al. | 702/190 |
| 6,678,548 B1 * | 1/2004 | Echauz et al. | 600/544 |

FOREIGN PATENT DOCUMENTS

| WO | WO0167288 | * | 6/2001 |
| WO | WO 01/67288 A2 | | 9/2001 |

OTHER PUBLICATIONS

L.M. Hively, P.C. Gailey, V.A. Protopopescu☐}Detecting dynamical change in nonlinear time series☐☐Jul. 19, 1999☐☐Elsevier Science B.V.☐☐.*

Hively, L.M. et al: "Detecting Dynamical Change in Nonlinear Time Series", Physics Letters A, Notrh-Holland Publishing Co., Amsterdam, NL, vol. 258, 1999, pp. 103-114, XP001051088, ISSN: 0375-9601.

Moeckel, R. et al: "Measuring The Distance Between Time Series", PHysica D Elsevier Netherlands, vol. 102, No. 3-4, 1997, pp. 187-194, XP002299927, ISSN: 0167-2789.

Abarbanel, H.D.I.: "The Analysis Of Observed Chaotic Data In Physical Systems", Reviews of Modern Physics, American Physical Society, US, vol. 65, No. 4, 1993-10, pp. 1331-1392, XP000937897, ISSN: 0034-6861.

L.M. Hively, P.C. Gailey, V.A. Protopopescu, Detecting dynamical change in nonlinear time series, Jul. 19, 1999, Physics Letters A, pp. 103-114; Oak Ridge, TN.

Anticipation of epileptic seizures from standard EEG recordings; The Lancet, vol. 357, Jan. 20, 2001; pp. 183-188.

* cited by examiner

*Primary Examiner*—Marc S. Hoff
*Assistant Examiner*—Leon Bathini, Jr.
(74) *Attorney, Agent, or Firm*—Quarles & Brady LLP

(57) ABSTRACT

This invention teaches further method improvements to forewarn of critical events via phase-space dissimilarity analysis of data from biomedical equipment, mechanical devices, and other physical processes. One improvement involves conversion of time-serial data into equiprobable symbols. A second improvement is a method to maximize the channel-consistent total-true rate of forewarning from a plurality of data channels over multiple data sets from the same patient or process. This total-true rate requires resolution of the forewarning indications into true positives, true negatives, false positives and false negatives. A third improvement is the use of various objective functions, as derived from the phase-space dissimilarity measures, to give the best forewarning indication. A fourth improvement uses various search strategies over the phase-space analysis parameters to maximize said objective functions. A fifth improvement shows the usefulness of the method for various biomedical and machine applications.

13 Claims, 5 Drawing Sheets

METHODS FOR CONSISTENT FOREWARNING OF CRITICAL EVENTS ACROSS MULTIPLE DATA CHANNELS

STATEMENT REGARDING FEDERALLY SPONSORED RESEARCH

This invention was made with assistance under Contract No. DE-AC05-00OR22725 with the U.S. Department of Energy. The Government has certain rights in this invention.

BACKGROUND OF THE INVENTION

The field of the invention is methods of computer analysis for forewarning of critical events, such as epileptic seizures in human medical patients, and mechanical failures in machines and other physical processes.

Hively et al., U.S. Pat. Nos. 5,743,860 and 5,857,978 disclose methods for detecting and predicting epileptic seizures by acquiring brain wave data from a patient, and analyzing the data with traditional nonlinear methods.

Many of the prior art methods of epileptic forewarning were based on intercranial electroencephalogram (EEG) data. The present invention can be practiced with EEG data obtained from sensors applied to the scalp of the patient. Prior advances using scalp EEG data removed artifacts with a zero-phase quadratic filter to permit analysis of single-channel scalp EEG data. Hively et al., U.S. Pat. No. 5,815,413, disclosed the use of phase space dissimilarity measures (PSDM) to forewarn of impending epileptic events from scalp EEG in ambulatory settings. Despite noise in scalp EEG data, PSDM has yielded superior performance over traditional nonlinear indicators, such as Kolmogorov entropy, Lyapunov exponents, and correlation dimension. However, a problem still exists in forewarning indicators, because false positives and false negatives may occur.

Hively et al., U.S. Pat. No. 5,815,413, also discloses the applicability of nonlinear techniques to monitor machine conditions such as the condition of a drill bit or the performance of an electrical motor driving a pump.

SUMMARY OF THE INVENTION

The present invention uses prior advances in the application of phase space dissimilarity measures to provide forewarning indications. In this method, a renormalized measure of dissimilarity, e.g., $U(\chi^2)$ or $U(L)$, is compared to a threshold value ($U_C$) and upon exceeding the threshold value for a sequential number of occurrences ($N_{occ}$), a forewarning indication is determined.

Forewarning indications are further resolved into true positives, true negatives, false positives and false negatives in multiple data sets taken from the same patient over multiple channels, where it is known whether the patients experienced biomedical events or did not experience such events. The results are then used to calculate a channel-consistent total true rate ($f_T$). This approach allows the observation of a channel or channels providing the largest channel-consistent total-true forewarning indications. Test data is then processed from the selected channel or channels to develop measures of dissimilarity and forewarning indications, which are most likely to be true forewarning indications.

Forewarning indications are used to forewarn of critical events, such as various biomedical events. Typical biomedical events and sources of data include, but are not limited to, epileptic seizures from EEG, cardiac fibrillation from EKG, and breathing difficulty from lung sounds.

The methods of the present invention also include determining a trend in renormalized measures, e.g., $U(\chi^2)$ or $U(L)$, based on phase space dissimilarity measures ($\chi^2$, L) for data sets collected during increasing fault conditions in machines or other physical processes. The invention then uses a "least squares" analysis to fit a straight line to the sum of the renormalized measures in order to forewarn of a critical event, such as a machine or process failure.

Typical machines include, but are not limited to, motors, pumps, turbines, and metal cutting. Typical time-serial machine data include, but are not limited to, electrical current, voltage, and power; position, velocity, and acceleration; and temperature and pressure. Other physical processes capable of being monitored by sensors can also be observed to forewarn of malfunctions or failures.

In the present invention, the data can also be analyzed to determine values for specific parameters that maximize the total true rate for one or more respective channels.

A further aspect of the invention enhances techniques by utilizing equiprobable symbols for computing the distribution functions from a connected or unconnected phase space.

Other objects and advantages of the invention, besides those discussed above, will be apparent to those of ordinary skill in the art from the description of the preferred embodiments, which follows. In the description reference is made to the accompanying drawings, which form a part hereof, and which illustrate examples of the invention. Such examples, however are not exhaustive of the various embodiments of the invention, and therefore reference is made to the claims, which follow the description for determining the scope of the invention.

DETAILED DESCRIPTION OF THE PREFERRED EMBODIMENTS

Figure 1:
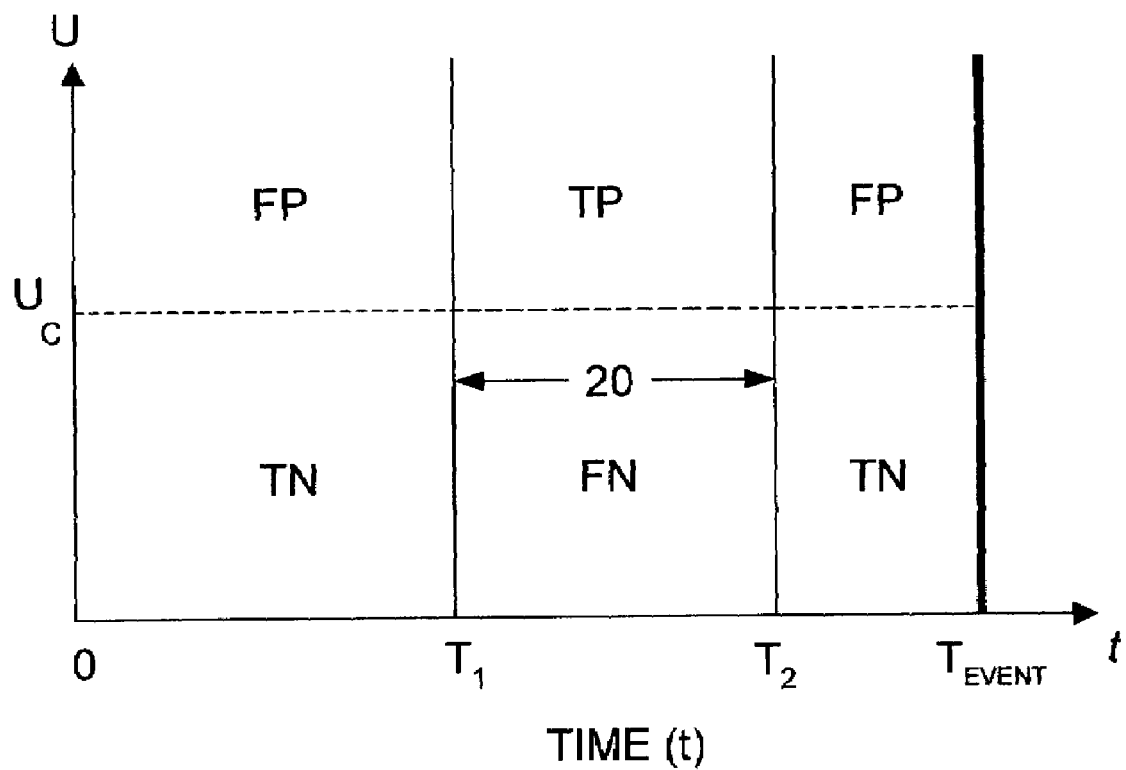
FIG. 1 is a graph of renormalized dissimilarity as a function of forewarning time (t) for determining true positive (TP), true negative (TN), false positive (FP) and false negative (FN) forewarning indications.

In a first embodiment of the present invention, a database of forty (40) data sets were collected, each with at least one electrographic temporal lobe (TL) event, as well as twenty (20) data sets without epileptic events, as controls. Data sets were obtained from forty-one (41) different patients with ages between 4 and 57 years. This data included multiple data sets from eleven (11) patients (for a total of 30 events), which were used for the channel consistency analysis. Such data can be collected (for example) with a 32-channel EEG instrument (Nicolet-BMSI, Madison, Wis.) with 19 scalp electrodes in the International 10–20 system of placement as referenced to the ear on the opposing hemisphere. Each channel of scalp potential was amplified separately, bandpass filtered between 0.5–99 Hz, and digitized at 250 Hz. The 19 EEG channels in each of these data sets had lengths between 5,016 seconds (1 hour and 23 minutes) and 29,656 seconds (8 hours and 14 minutes).

The following description incorporates the methods first disclosed in Hively, U.S. patent application Ser. No. 09/520,693, filed Mar. 7, 2000 and now pending. To the extent that the methods of the present invention build upon the methods disclosed there, the disclosure of that application is hereby incorporated by reference.

In the present invention, eye blink artifacts from scalp EEG are removed with a zero-phase quadratic filter that is more efficient than conventional linear filters. This filter uses a moving window of data points, $e_i$, with the same number of data points, w, on either side of a central point. A quadratic curve is fitted to these 2w+1 data points, taking the central point of the fit as the low-frequency artifact, $f_i$. The residual, $g_i = e_i - f_i$, has essentially no low-frequency artifact activity. All subsequent analysis uses this artifact-filtered data.

Next, each next artifact-filtered value is converted into a symbolized form, $s_i$, that is, one of S different integers, 0, 1, . . . , S−1:

$$0 \leq s_i = INT[S(g_i - g_{min})/(g_{max} - g_{min})] \leq S-1. \quad (1)$$

The function INT converts a decimal number to the closest lower integer; $g_{min}$ and $g_{max}$ denote the minimum and maximum values of $g_i$, respectively, over the base case (reference data). To maintain S distinct symbols, the following expression holds, namely $s_i = S-1$ when $g_i = g_{max}$. Expression (1) creates symbols that are uniformly spaced between the minimum and maximum in signal amplitude (uniform symbols). Alternatively, one can use equiprobable symbols, by ordering all N base case data points from the smallest to the largest value. The first N/S of these ordered data values correspond to the first symbol, 0. Ordered data values (N/S)+1 through 2N/S correspond to the second symbol, 1, and so on up to the last symbol, S−1. By definition, equiprobable symbols have non-uniform partitions in signal amplitude and present the advantage that dynamical structure arises only from the phase-space reconstruction. Moreover, large negative or positive values of $g_i$ have little effect on equiprobable symbolization, but significantly change the partitions for uniform symbols. Finally, the mutual information function is a smooth function of the reconstruction parameters for equiprobable symbols, but is a noisy function of these same parameters for uniform symbols. Thus, equiprobable symbols provide better discrimination of condition change than uniform symbols when constructing a connected phase space.

Phase-space (PS) construction uses time-delay vectors, $y(i) = [s_i, s_{i+\lambda}, \ldots, s_{i+(d-1)\lambda}]$ to unfold the underlying dynamics. Critical parameters in this approach are the time delay, $\lambda$, and system dimensionality, d, and the type and number of symbols, S. Symbolization divides the phase space into $S^d$ bins. The resulting distribution function (DF) is a discretized density on the attractor, which is obtained by counting the number of points that occur in each phase space bin. The population of the ith bin of the distribution function, is denoted $Q_i$, for the base case, and $R_i$ for a test case, respectively. The test case is compared to the base case by measuring the difference between $Q_i$ with $R_i$ as:

$$\chi^2 = \sum_i (Q_i - R_i)^2 / (Q_i + R_i), \quad (2)$$

$$L = \sum_i |Q_i - R_i|, \quad (3)$$

Here, the summations run over all of the populated phase space cells. These measures account for changes in the geometry, shape, and visitation frequency of the attractor, and are somewhat complementary. The $\chi^2$ measure is one of the most powerful, robust, and widely used statistics for comparison between observed and expected frequencies. In this context, $\chi^2$ is a relative measure of dissimilarity, rather than an unbiased statistic for accepting or rejecting a null statistical hypothesis. The L distance is the natural metric for distribution functions by its direct relation to the total invariant measure on the attractor and defines a bona fide distance. Consistent calculations of these measures obviously require the same number of points in both the base case and test case distribution functions, identically sampled; otherwise, the distribution functions must be properly rescaled.

The connected PS is constructed by connecting successive PS points as prescribed by the underlying dynamics, $y(i) \to y(i+1)$. Thus, a discrete representation of the process flow is obtained in the form of a 2d-dimensional vector, $Y(i) = [y(i), y(i+1)]$, that is formed by adjoining two successive vectors from the d-dimensional reconstructed PS. Y(i) is a vector for the connected phase space (CPS). As before, Q and R denote the CPS distribution functions for the base case and test case, respectively. The measure of dissimilarity between the two distribution functions for the CPS, signified by the "c" subscript are thus defined as follows:

$$\chi_c^2 = \sum_{ij} (Q_{ij} - R_{ij})^2 / (Q_{ij} + R_{ij}) \quad (4)$$

$$L_c = \sum_{ij} |Q_{ij} - R_{ij}|. \quad (5)$$

The first subscript in Eqs. (4)–(5) denotes the initial PS point, and the second subscript denotes the sequel PS point in the PS pair. These CPS measures have higher discriminating power than unconnected PS measures of dissimilarity. Indeed the measures defined in Eqs. (4)–(5) satisfy the following inequalities: $\chi^2 \leq L$, $\chi_c^2 \leq L_c$, $L \leq L_c$, and $\chi^2 \leq \chi_c^2$, where $\chi_c^2$ and $L_c$ are dissimilarity measures for connected phase space and $\chi^2$ and $L$ are dissimilarity measures for unconnected PS.

To assure robustness, the construction of the base case data requires careful statistics to eliminate outlier base case cutsets. The first B non-overlapping windows of N points (cutsets) for each dataset become the base case cutsets. A few of these base case cutsets can be very atypical, causing a severe bias in the detection of condition change. The base case cutsets are tested for outliers as follows. A comparison of the B(B−1)/2 unique pairs among the B base case cutsets via Eqs. (2)–(5) yields dissimilarities, from which we obtain an average, $\underline{V}$, and sample standard deviation, $\sigma$, for each of the four measures of dissimilarity, $V=\{L, L_c, \chi^2, \text{ and } \chi_c^2\}$, where the subscript, c, denotes the measures of dissimilarity for the CPS. Then, a $\chi_j^2$ statistic, $\chi_j^2=\Sigma_i(V_{ij}-\underline{V})^2/\sigma$, is calculated for each of these four dissimilarity measures. The index i runs over the B non-overlapping basecase cutsets. The index j is fixed, to test the jth cutset against the other B−1 cutsets, thereby giving B−1 degrees of freedom in the $\chi_j^2$ statistic. The null statistical hypothesis allows a random outlier with a probability less than 2/B(B−1). If this hypothesis is not satisfied, we identify an outlier cutset as having $\chi_j^2>19.38$ for at least one of the four dissimilarity measures, which corresponds to a probability larger than 1/45 for B=10. If this analysis does not identify an outlier, then the previous values of V and $\sigma$ are used for subsequent renormalization, as described below. If this analysis identifies an outlier, the cutset is removed. The analysis is repeated with a new value, B=9 for the remaining base case cutsets to identify any additional outliers. Their presence is indicated by the largest $\chi_j^2$ statistic exceeding the new threshold of 17.24, corresponding to a random probability larger than 1/36, as interpolated from standard statistical tables for 8 degrees of freedom. Rejection of the null hypothesis for even fewer remaining cutsets (degrees of freedom) corresponds to a $\chi_j^2$ statistic larger than 15.03, 12.74, and 10.33, for B=8, 7, and 6, respectively. If the analysis identifies five (or more) outliers, we would have to reject all of the base cases as unrepresentative, and acquire a new set of ten cutsets as base cases. However, in the present analysis, more than four outliers were not seen.

The disparate range and variability of these measures are difficult to interpret for noisy EEG, so a consistent method of comparison is needed. To this end, the dissimilarity measures are renormalized, as described below. The B non-outlier base case cutsets are compared to each test case cutset, to obtain the corresponding average dissimilarity value, $V_i$, of the ith cutset for each dissimilarity measure. Here, V denotes each dissimilarity measure from the set, $V=\{L, L_c, \chi^2, \text{ and } \chi_c^2\}$. The mean value, $\underline{V}$, and the standard deviation, $\sigma$, of the dissimilarity measure V are calculated using the remaining base case cutsets, after the outliers have been eliminated, as discussed above. The renormalized dissimilarity is the number of standard deviations that the test case deviates from the base case mean: $U(V)=|V_i-\underline{V}|/\sigma$.

Once the renormalized measures for the test and base cases have been obtained, a threshold, $U_C$, is selected for each renormalized measure U to distinguish between normal (base) and possibly abnormal (test) regimes. The choice of a reasonable threshold is critical for obtaining robust, accurate, and timely results. A forewarning indication is obtained when a renormalized measure of dissimilarity exceeds the threshold, $U \geq U_C$, for a specified number, $N_{OCC}$, of sequential occurrences within a preset forewarning window.

According to the present invention, and as illustrated in FIG. 1, $N_{OCC}$ sequential occurrences above the threshold ($U>U_C$) are interpreted as a forewarning indication. Such forewarning indications are true positives, TP, if they occur within a forewarning window 20. Other performance metrics include true negatives, TN, false positives, FP, and false negatives, FN, also defined with respect to the same preset forewarning window, as shown in FIG. 1. The horizontal axis represents time, t. The thick vertical line at $T_{EVENT}$ denotes an event onset time. The thin vertical lines delimit the forewarning-time window 20, during which $T_1 \leq t \leq T_2 < T_{EVENT}$. For illustration, "reasonable" forewarning windows are set at $T_1 = T_{EVENT}-60$ min and $T_2 = T_{EVENT}-1$ min, for biomedical events. A typical forewarning window for machine failure is on the order of either hours or days. The vertical axis corresponds to a renormalized measure of dissimilarity, U, as discussed above. The horizontal dashed line (--) shows the threshold, $U_C$. A forewarning time in one channel, $T_{FW}$, is that time when the number of simultaneous indications, $N_{SIM}$, among the four dissimilarity measures exceeds some minimum value. The best elimination of FPs occurs for a value of $N_{SIM}=4$. Analysis starts at t=0, and proceeds forward in time until the first forewarning occurs, as defined above. The algorithm then obtains the forewarning statistics by an ordered sequence of logical tests for each channel:

FP=false positive=forewarning at any time, when no event occurs, or forewarning with $T_{FW}<T_1$, or $T_{FW}>T_2$, for an event at $t=T_{EVENT}$;

TP=true positive=forewarning with $T_1 \leq T_{FW} \leq T_2$ for an event at $t=T_{EVENT}$;

TN=true negative=no forewarning, when no event occurs; and

FN=false negative=no forewarning for $t \leq T_{EVENT}$ with an event at $t=T_{EVENT}$.

The i-th dataset is referred to as TP if at least one channel shows forewarning within the desired window, $T_1 \leq T_{FW} \leq T_2$. This indication is equivalent to $TP_i=1$ in the equations below. A TN dataset shows no forewarning in at least one channel when no event occurs. This indication is equivalent to $TN_i=1$ in the equations below. The total true rate, $T=\Sigma_i(TP_i+TN_i)/\Sigma_i(TP_i+TN_i+FP_i+FN_i)$, and the total false rate, $F=\Sigma(FP_i+FN_i)/\Sigma_i(TP_i+TN_i+FP_i+FN_i)$, where the sums run over all data sets. This approach allows selection of an appropriate channel for subsequent real-time forewarning, consistent with the previous characterization of the data.

Improvement in the channel-consistent total-true rate is carried out by maximizing an objective function that measures the total true rate for any one channel, as well as channel consistency. For this analysis, 30 data sets were used from 11 different patients with multiple data sets as follows: 7 patients with 2 data sets, one patient with 3 data sets, 2 patients with 4 data sets, and one patient with 5 data sets. To quantify channel consistency, the following notation and definitions are used:

i=dataset number;

j=channel number in which forewarning is determined ($1 \leq j \leq 19$);

k=patient number;

M(k)=number of data sets for the k-th patient;

P=number of patients with multiple data sets (eleven for the present analysis);

$TN_{ijk}=1$ for a true negative indication in the j-th channel of the i-th dataset for the k-th patient, and =0 for a false negative indication in the j-th channel of the i-th dataset for the k-th patient;

$TP_{ijk}=1$ for a true positive indication in the j-th channel of the i-th dataset for the k-th patient, and =0 for a false positive indication in the j-th channel of the i-th dataset for the k-th patient.

The total-true rate for the j-th channel of the k-th patient is $T_{jk}=\Sigma_i[TP_{ijk}+TN_{ijk}]$, by summing over the datasets, i=1 to M(k). The occurrence of more than one true positive and/or true negative in the j-th channel is indicated by $T_{jk} \geq 2$, while $T_{jk} \leq 1$ means that the j-th channel provides no consistency with other data sets for the same patient. Consequently, the channel overlap is defined as:

$$c_k = \max(T_{jk}), \text{ for } T_{jk} \geq 2 \text{ and } k \text{ fixed},$$
$$= 0, \text{ for } T_{jk} \leq 1.$$

The channel-consistent total-true rate is the average, $f_T = [\Sigma_k c_k]/[\Sigma_k M(k)]$, where the index, k, sums over all P patients, weighting each dataset equally. If the channel-consistent total-true rate had been defined as $[\Sigma_k \max(T_{jk})/M(k)]/P$, then patients with only one dataset would have been improperly weighted the same as patients with several data sets). For selected values of the parameters (e.g., N, w, S, d), the renormalized measures of PS dissimilarity are computed with these parameters for each dataset, and then exhaustively searched over $N_{OCC}$ and $U_C$ to find the largest $f_T$ value.

FIGS. 2a–2d illustrate a series of single parameter searches to maximize the channel-consistent total-true rate for forewarning of epileptic seizures. The value of one parameter is systematically changed, while the others are fixed. In this example, the first-round optimization uses the parameter pair, {S, d}, constrained by a computational limit on the numeric labels for the CPS bins using modular arithmetic. This limit arises from the largest double-precision real number $2^{52}$ that can be distinguished from one unit larger: $S^{2d} \leq 2^{52}$, or $d \leq INT(26\ln 2/\ln S)$. Two PS symbols (S=2) limit the search to $2 \leq d \leq 26$; three PS symbols (S=3) correspond to $2 \leq d \leq 16$; and so forth. Since equiprobable symbols always yield larger values for $f_T$, the analysis in this example was performed using this symbolization.

Figure 2A:
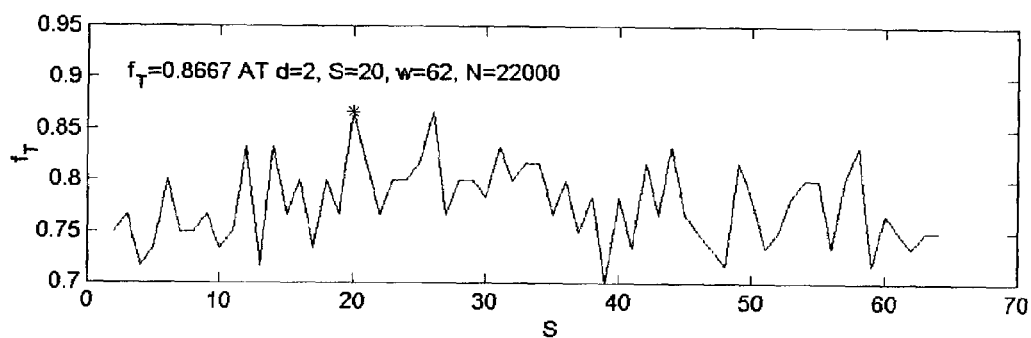
FIGS. 2a–2d are graphs of channel-consistent total-true rates for forewarning of epileptic seizures, $f_T$ vs. selected parameters: (a) $f_T$ versus S (number of phase space symbols) for d=2, w=62, N=22,000; (b) largest $f_T$ versus d (number of phase space dimensions) for w=62, N=22,000 using equiprobable symbols (solid curve) and uniform symbols (dash-dot curve); (c) $f_T$ versus w (half width of the artifact-filter window width) for d=2, S=20, N=22,000; and (d) $f_T$ versus N (number of data points in each cutset) for d=2, S=20, and w=54.
Figure 2B:
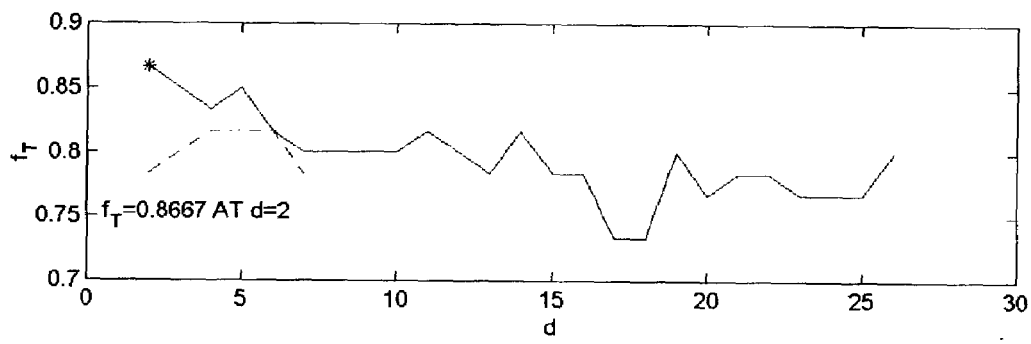
Figure 2C:
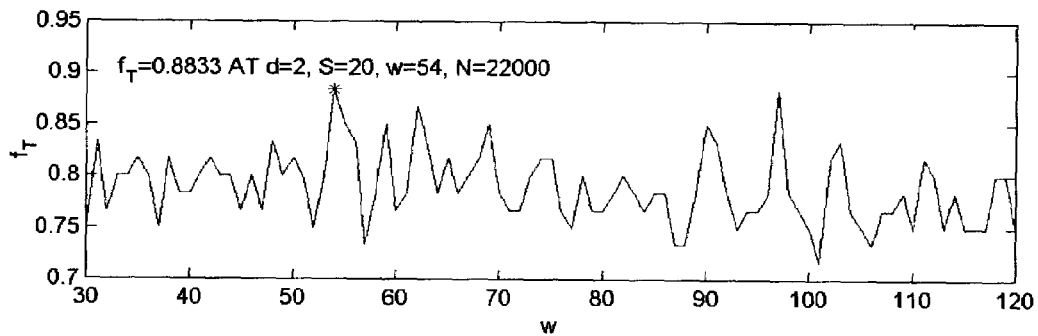
Figure 2D:
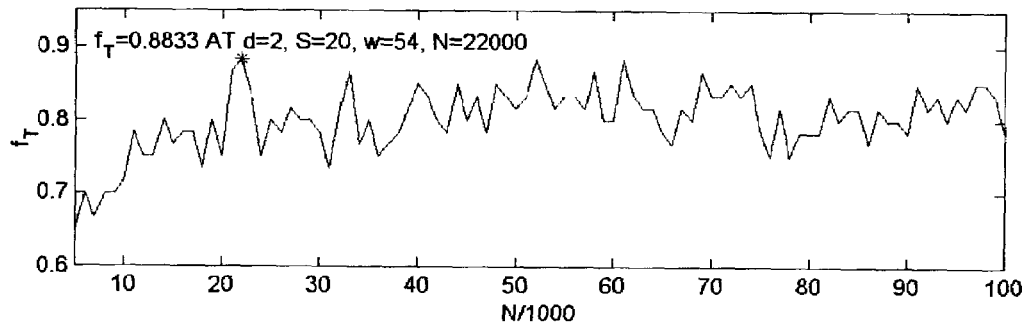
Figure 3A:
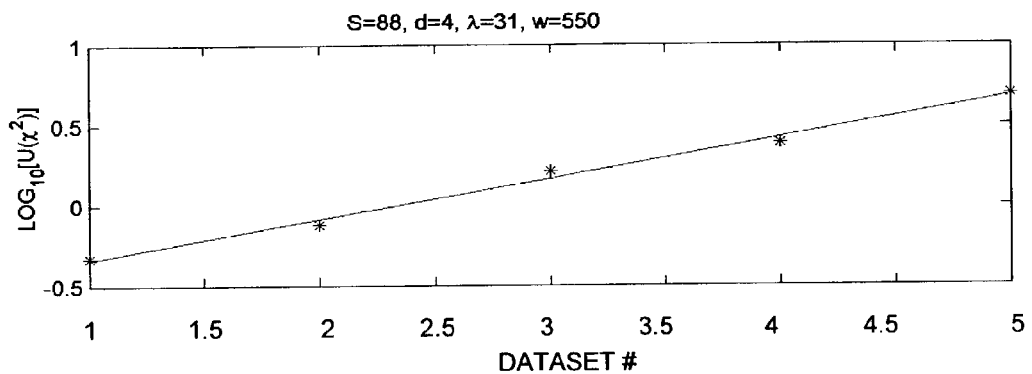
FIGS. 3a–3d are semi-$\log_{10}$ plots of the four nonlinear dissimilarity measures for a set of broken-rotor seeded-fault power data. Dataset #1 is for the nominal (no fault) state. Dataset #2 is for the 50% cut in one rotor bar. Dataset #3 is for the 100% cut in one rotor bar. Dataset #4 is for two cut rotor bars. Dataset #5 is for four cut rotor bars. The exponential rise in the severity of the seeded faults is shown as an almost linear rise (solid line) in the logarithm of all four dissimilarity measures (*) for the chosen set of phase-space parameters.
Figure 3B:
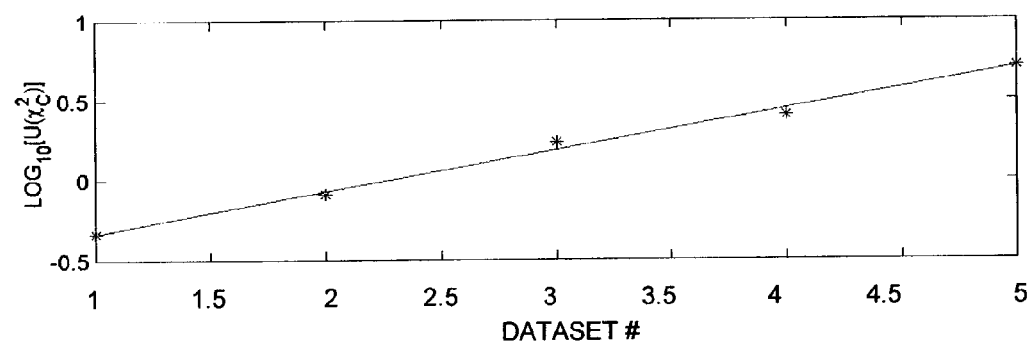
Figure 3C:
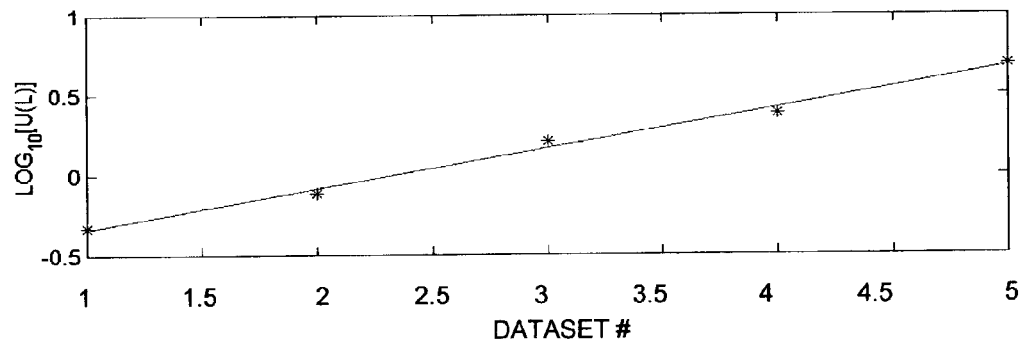
Figure 3D:
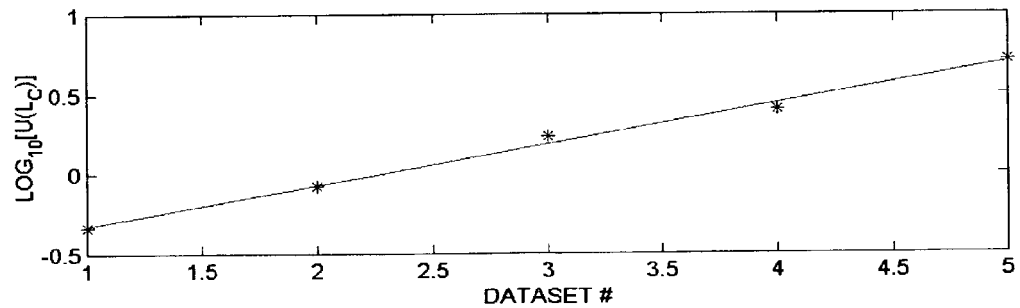

FIG. 2a shows $f_T$ as a noisy function of the number of equiprobable symbols, S, with the number of PS dimensions, d=2. The largest channel-consistent total-true rate is $f_T=0.8667$ at S=20 and S=26. Next, the largest value of $f_T$ was obtained over all of the possible equiprobable symbols for each value of PS dimension in the range, $2 \leq d \leq 26$. These results are displayed as the solid curve in FIG. 2b, showing that $f_T$ decreases non-monotonically from a maximum at d=2 to a minimum at d=17–18, and then rises somewhat for still larger values of d. For completeness, FIG. 2b also shows similar analysis only for an even number of uniform symbols (dash-dot curve), because the central bin for an odd number of uniform symbols accumulates the vast majority of the PS points, thus degrading the results in every case. Based on these results, further analysis for uniform symbols is unnecessary. Thus, we set d=2 and S=20 (equiprobable symbols) while varying the half-width of the artifact filter window, w, as shown in FIG. 2c. It is observed that $f_T$ also is a noisy function of w with a maximum value of $f_T=0.8833$ at w=54 and w=98. The former value (w=54) is selected for the next parameter scan, because a slight trend for larger $f_T$ lies in that region. FIG. 2d displays $f_T$ versus the number of points in each cutset, N, in increments of 1000 with the other parameters fixed at S=20, d=2, and w=54. This plot shows that $f_T$ rises non-monotonically with increasing cutset length to a noisy plateau for N>21,000. The largest value, $f_T=0.8833$, occurs at N=22,000; N=54,000, and N=61,000. All of the above analysis used a time delay, $\lambda=INT[0.5+M_1/(d-1)]$, which in general is different for every channel of each dataset, as discussed previously. However, this parameter also is a variable. Consequently, the variation of $f_T$ was determined as a function of the time delay, $\lambda$, which was set to the same value for every channel of every dataset. A single peak occurs at $f_T=0.9$ for $\lambda=17$, with the other parameters fixed at S=20, d=2, w=54, and N=22 000.

The above results show that a substantial improvement in the rate of channel-consistent total trues ($f_T=0.9$) is obtained for sub-optimal choices of the analysis parameters. Moreover, the new set of analysis parameters yielded credible event forewarning (29 total trues) for solitary data sets from each of 30 different patients. It is expected that a robust choice of the parameters can be obtained by analysis of much more data, and subsequently fixed for an ambulatory device. Alternatively, initial clinical monitoring might be used to determine the best patient-specific analysis parameters, which would be fixed subsequently for ambulatory monitoring. This sequence of single parameter searches for maximizing the objective function was necessary because the computational effort for an exhaustive search is excessive. However, a small amount of experimental data or very narrow parameter ranges make an exhaustive parameter search feasible, as one normally skilled in the art can appreciate.

The best choice of the parameter set for analyzing the dissimilarity measures for each channel, (e.g., N, w, S, d, B, $N_{OCC}$, and $U_C$), depends not only on the system, but also on the specific data under consideration. A "reasonable" value for the number of base case cutsets, $5 \leq B \leq 10$, was selected as a balance between a reasonably short quasi-stationary period of "normal" dynamics and a sufficiently long period for statistical significance. This method of the present invention involves: selecting the parameters to be included in a parameter set, such as {N, w, S, and d}, finding specific values for the parameters that maximize the objective function for the respective channels, computing the renormalized measures of PS dissimilarity for the specific data sets with the parameters set to their best values, and systematically searching over the values of $N_{OCC}$ and $U_C$ to find the best channel for forewarning indication.

Besides epileptic seizures, the above methods can be applied to detect condition change in patients having cardiac or breathing difficulties.

The above methods can also be applied to electric motor predictive maintenance, other machinery, and physical processes. In the second example, data sets were recorded in snapshots of 1.5 seconds, sampled at 40 kHz (60,000 total time-serial samples), including three-phase voltages and currents, plus tri-axial accelerations at inboard and outboard locations on a three-phase electric motor. The subsequent description describes analysis of one seeded fault.

The test sequence began with the motor running in its nominal state (first dataset), followed by progressively more severe broken rotor bars. The second dataset involved a simulated failure that was one rotor bar cross section cut through by 50%. The third dataset was for the same rotor bar now cut through 100%. The fourth dataset was for a second rotor bar cut 100%, exactly 180° from and in addition to the first rotor fault. The fifth dataset was for two additional rotor bars cut adjacent to the first rotor bar, with one bar cut on each side of the original, yielding four bars completely open. These five datasets were concatenated into a single long dataset for ease of analysis. The three-phase voltages, $V_i$, and currents, $I_i$, were converted into instantaneous power, $P=\Sigma_i I_i V_i$, where the sum runs over the three phases. We split each of the five datasets into five subsets of 12,000 points each, giving twenty-five (25) total subsets. The power has a slow, low-amplitude variation with a period of roughly 0.1 s. To avoid confounding the analysis, this artifact was removed with the zero-phase quadratic filter.

The PS reconstruction parameters were systematically varied, as before, to obtain the most linear increase in the logarithm of condition change, in a least-squares sense, for the broken-rotor test sequence. FIG. 3 shows that the phase-space dissimilarity measures rise by ten-fold over the test sequence. The parameters are: S=88 (number of equiprobable phase-space symbols), d=4 (number of phase-space dimensions), $\lambda$=31 (time delay lag in time steps), and w=550 (half width of the artifact filter window in time steps). The exponential rise in the severity of the broken-rotor faults (doubling from 0.5 to 1.0 to 2.0 to 4.0) is mirrored in FIGS. 3a–3d by a linear rise (solid line) in the logarithm of all four dissimilarity measures (*) for the chosen set of analysis parameters.

The present invention not only responds to the problem of false positives and false negatives in forewarning of events from biomedical data, but also is also applicable to forewarning of machine failures and even failures in other physical processes capable of being measured through sensors and transducers.

A third example involves tri-axial acceleration data from a motor connected to a mechanical load via a gearbox. Application of excess load causes accelerated failure of the gears. The data were obtained at ten-minute intervals through the test sequence, sampled at 102.4 kHz. The total amount of data was 4.5 GB (three accelerometer channels, times 401 snapshots for a total of 1203 files). The 100,000 data points were serially concatenated from each of the data files into a single three-channel dataset for ease of analysis (1.6 GB). Each 100,000-point snapshot was divided into ten 10,000-point subsets for this analysis; the results were then averaged over these ten cutsets to obtain a typical value for the entire snapshot. The accelerometer data shows quasi-periodic, complex, nonlinear features.

The use of tri-axial acceleration has an important advantage, which can be explained as follows. Acceleration is a three-dimensional vector that can be integrated once in time to give velocity (vector). Mass times acceleration (vector) is force (vector). The vector dot-product of force and velocity is power (scalar). Thus, three-dimensional acceleration data can be converted directly into a scalar power (within a proportionality constant), which captures the relevant dynamics and has more information about the process than any single accelerometer channel. The resulting accelerometer power also has very complex, nonlinear features.

Figure 4:
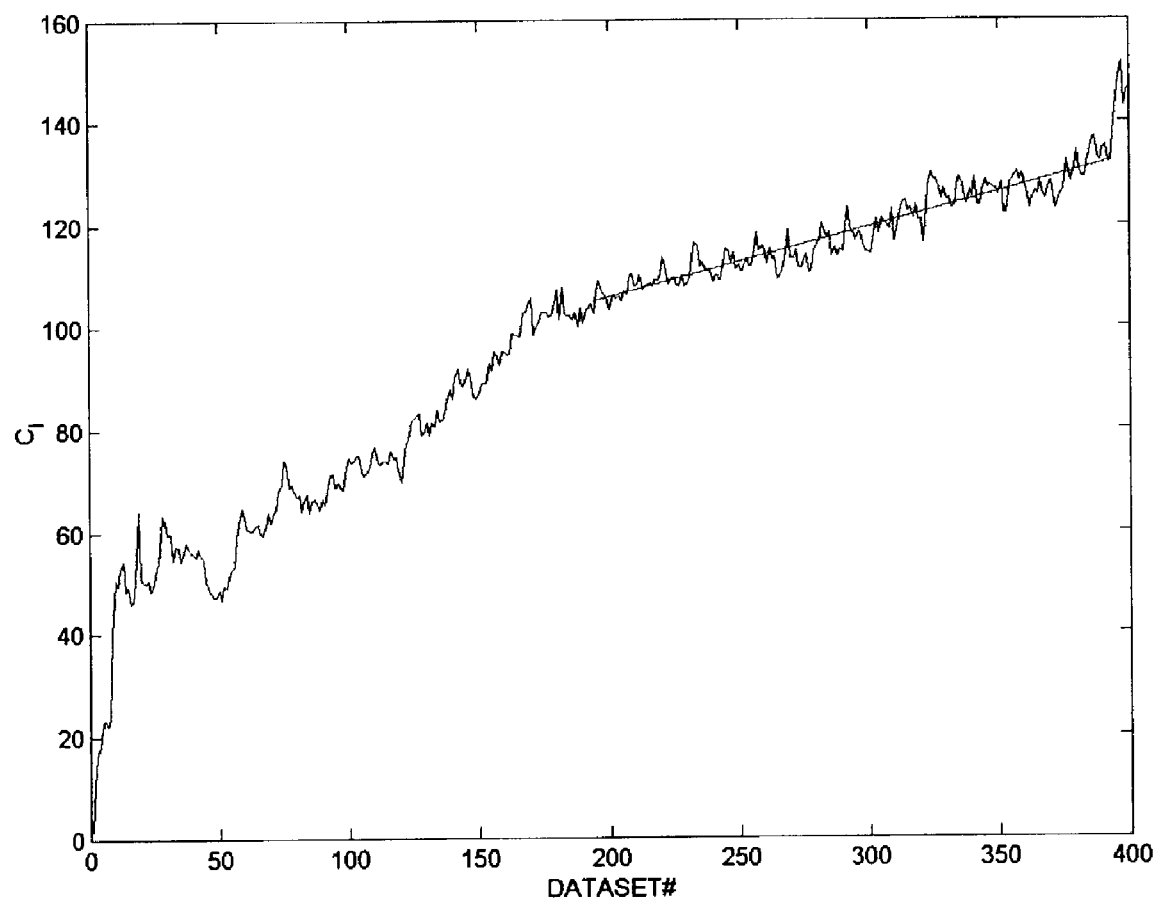
FIG. 4 is a plot of the composite PS dissimilarity measure, $C_i$, versus dataset number for a gearbox failure (d=2, S=274, and λ=1).

FIG. 4 shows a systematic rise in a composite PS dissimilarity of accelerometer power as the test progresses, with an additional abrupt rise at the onset of failure, which occurs at dataset #394. This result was obtained by constructing a composite measure, $C_i$, of condition change, namely the sum of the four renormalized measures of dissimilarity in accelerometer power for each of the datasets in the test sequence. The following method was used to obtain this result:

1) Construct a composite measure, $C_i = U(\chi^2) + U(\chi_c^2) + U(L) + U(L_C)$, for the i-th dataset;

2) Fit $C_i$ to a straight line, $y_i = ai+b$ via least-squares over a window of m datasets (datasets #194–393 in this case), also shown in FIG. 4;

3) Obtain the variance, $\sigma_1^2 = \Sigma_i (y_i - C_i)^2/(m-1)$, of $C_i$ about the straight-line fit from step 2;

4) Determine the statistic, $\chi^2 = \Sigma_i (y_i - C_i)^2/\sigma_1^2$, from this straight-line fit for datasets #394–400;

5) Maximize the value of $\chi^2$ from step 4 over the parameters (d, S, $\lambda$).

The variance, $\sigma_1^2$, in step 3 measures the variability of $C_i$ about the straight-line fit over the window of m datasets (#194–393).

Figure 5:
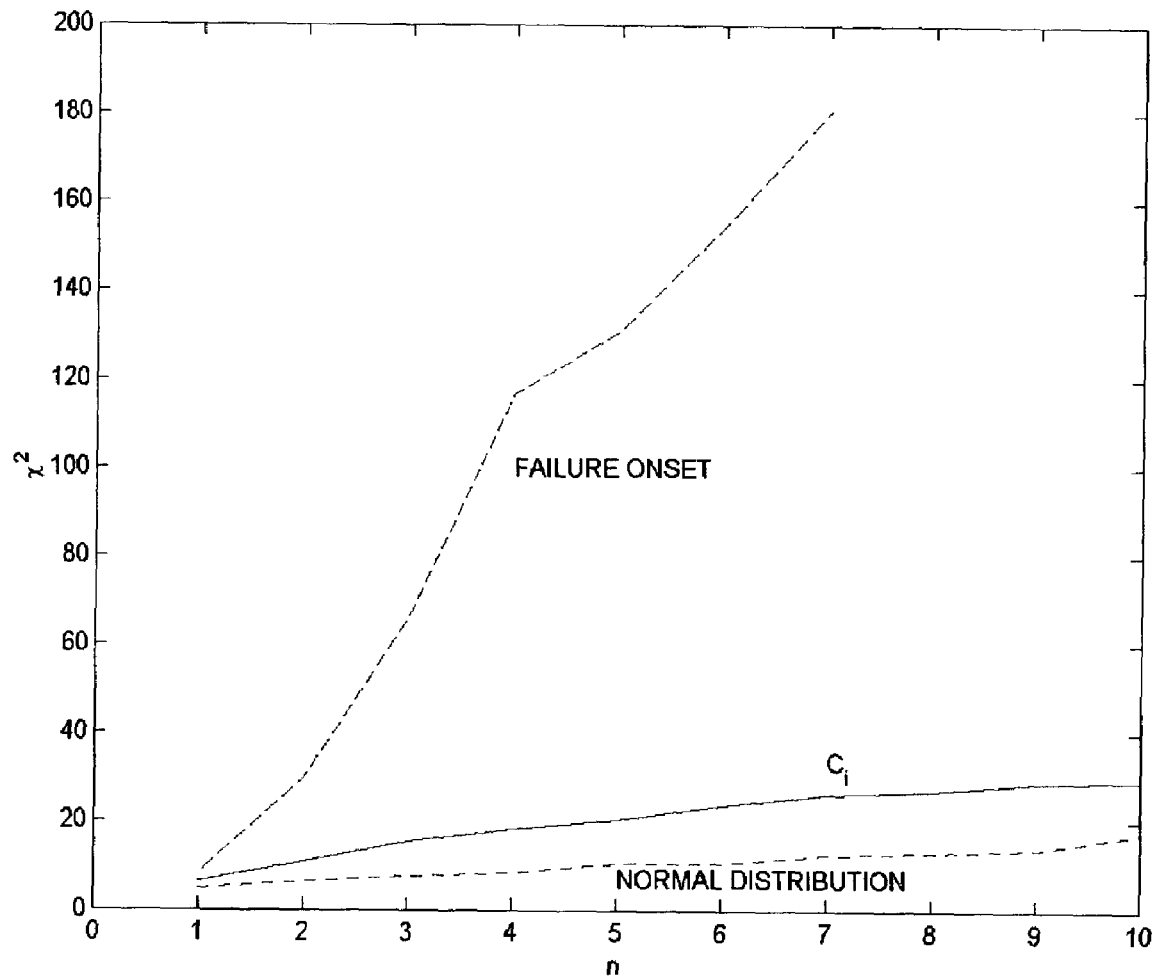
FIG. 5 is a plot of the maximum value of the $\chi^2$ statistic versus the number (n) of sequential points from the sample distribution for (bottom) a normal distribution with zero mean and unity sample standard deviation; (middle) composite measure, $C_i$, of condition change from the 200 datasets that span the straight-line fit; (top) composite measure, $C_i$, of condition change during failure onset (datasets #394–400). The middle and top curves use the same analysis parameters as in FIG. 4.

The statistic, $\chi^2$, in step 4 measures the variability of datasets #394–400 from the straight-line fit. The value from step 4 is $\chi^2$=180.42, which is inconsistent with a normal distribution for n=7 degrees of freedom (corresponding to the seven datasets in the computation of the $\chi^2$ statistic in step 4), and is a strong indication of the failure onset. Indeed, FIG. 5 shows a clear statistical indication of failure onset. The bottom plot (labeled "normal distribution") in FIG. 5 depicts the maximum value of the $\chi^2$ statistic for n sequential values out of 200 samples from a Gaussian (normal) distribution with zero mean and a unity sample standard deviation. The middle curve in FIG. 5 is the maximum value of the $\chi^2$ statistic, using step 4 above, for n sequential values of the composite measure, $C_i$, over the window of m=200 datasets that span the straight-line fit (datasets #194–393). The upper curve in FIG. 5 is the $\chi^2$ statistic, also using step 4 above, for n sequential values from datasets #394–400. This upper curve (labeled "failure onset") deviates markedly from the lower curves after two datasets (#394–395), with overwhelming indication for three and more datasets. Thus, the composite PS dissimilarity measure provides an objective function that shows consistent indication of condition change, as well as clear indication of the failure onset.

The fourth and final example used the same overloaded gearbox test bed, as in the third example. A separate test sequence acquired load torque that was sampled at 1 kHz. Each ten-second dataset had 10,000 data points, all of which were concatenated serially into a single data file for ease of analysis. These data are quasi-periodic with complex, nonlinear features. The analysis parameters were varied, as described above, to obtain phase-space dissimilarity measures that remain below a threshold for datasets #1–29. All four dissimilarity measures subsequently rise, beginning at dataset #30, and remain above threshold (U>$U_C$=0.894) for the remainder of the test sequence until final failure at dataset #44. These results illustrate that the phase-space dissimilarity measures can provide forewarning of an impending machine failure, not unlike the first example for forewarning of an epileptic event from EEG data.

This has been a description of detailed examples of the invention. These examples illustrate the technical improvements, as taught in the present invention: use of equiprobable symbols, quantitification of channel-consistent total-true rate of forewarning, various objective functions for event forewarning, different search strategies to maximize these objective functions, and forewarning of various biomedical events and failures in machines and physical processes. Typical biomedical events and data include, but are not limited to, epileptic seizures from EEG, cardiac fibrillation from EKG, and breathing difficulty from lung sounds. Typical machines include, but are not limited to, motors, pumps, turbines, and metal cutting. Typical time-serial machine data include, but are not limited to, electrical current, voltage, and power; position, velocity, and acceleration; and temperature and pressure. It will apparent to those of ordinary skill in the art that certain modifications might be made without departing from the scope of the invention, which is defined by the following claims.

I claim:

1. A method for processing data to provide a forewarning of a critical event, comprising:
   acquiring a plurality of sets of data with a plurality of channels of data for at least one test subject or process;
   computing a renormalized measure of dissimilarity for distribution functions derived from a connected phase space for each respective channel of data;
   comparing said renormalized measure of dissimilarity to a threshold ($U_C$) for a number of occurrences ($N_{OCC}$) to indicate a condition change in said renormalized measure of dissimilarity;
   detecting a simultaneous condition change in a plurality ($N_{SIM}$) of renormalized measures of dissimilarity to determine a forewarning of the critical event;
   determining true positive, true negative, false positive and false negative indications of condition change forewarning of the critical event for each channel of data in the plurality of sets of data;
   calculating a total true rate for forewarning indications for each channel of data; and
   comparing the total true rates for respective channels to determine at least one channel with a greatest channel-consistent total-true rate in said at least one channel.

2. The method of claim 1, wherein the test subject is a human patient.

3. The method of claim 1, wherein the test subject is a mechanical device or physical process.

4. The method of claim 1, further comprising:
   testing a plurality of parameters for each channel to determine optimum values for parameters corresponding to a highest channel-consistent total-true rate for a respective channel; and
   setting the plurality of parameters to the optimum values for processing data from other channels of data.

5. The method of claim 1, wherein the connected phase space is constructed by computing equiprobable symbols for the data in the data sets.

6. The method of claim 1, wherein the total true rate is calculated as $\Sigma_i(TP_i+TN_i)/\Sigma_i(TP_i+TN_i+FP_i+FN_i)$, where TP are true positives, TN are true negatives, FP are false positives and FN are false negative forewarning indications and wherein "i" is the data set number.

7. The method of claim 1, further comprising determining a sequence of renormalized phase space dissimilarity measures from data sets collected during increasingly severe fault conditions; summing said renormalized measures into a composite measure, $C_i$, for an i-th data set; performing a least-squares analysis over a window of m points of the said composite measure to obtain a straight line, $y_i=ai+b$, that best fits said composite data in a least-squares sense; determining a variance, $\sigma_1^2=\Sigma_i(y_i-C_i)^2/(m-1)$, of said composite measure with respect to the straight line fit; obtaining the variance of a sequel window of n sequential points via a statistic, $\chi^2=\Sigma_i(y_i-C_i)^2/\sigma_1^2$; comparing said value of $\chi^2$ to a maximal value of the same statistic, $\chi^2(C_i)$ for a window of n sequential points from said $C_i$ values; and determining an onset of a critical event, such as a machine failure, when $\chi^2$ is significantly more than $\chi^2(C_i)$.

8. The method of claim 1, further comprising:
   selecting a set of parameter values (N, w, S, and d) for computing the measures of dissimilarity for distribution functions in connected phase space for the data sets to be processed; and
   searching over the values of the forewarning threshold ($U_C$) and a corresponding number of occurrences ($N_{OCC}$) for each channel to find a best channel for forewarning indication.

9. The method of claim 8, wherein the connected phase space is constructed by computing equiprobable symbols for the data in the data sets.

10. The method of claim 1, wherein
    a plurality of renormalized measures of dissimilarity are computed for distribution functions derived from a connected phase space for each respective channel of data; and
    wherein said plurality of renormalized measures of dissimilarity are compared to respective thresholds to indicate respective condition change forewarning of the critical event.

11. The method of claim 10, wherein
    a second plurality of renormalized measures of dissimilarity are also computed for distribution functions derived from an unconnected phase space for each respective channel of data; and
    wherein said second plurality of renormalized measures of dissimilarity are compared to respective thresholds to indicate respective condition change forewarning of the critical event.

12. The method of claim 1, wherein
    a plurality of renormalized measures of dissimilarity are computed for distribution functions derived from a connected phase space for each respective channel of data;
    wherein said renormalized measures of dissimilarity are summed to provide a composite measure of dissimilarity; and
    wherein said composite measure of dissimilarity is compared to a threshold to indicate a respective condition change forewarning of the critical event.

13. The method of claim 12, further comprising:
    computing a chi-squared statistic, $\chi^2=\Sigma_i(y_1-C_i)^2/\sigma_1^2$, for the composite dissimilarity measure;
    testing a plurality of parameters for each channel to determine optimum values for parameters corresponding to a largest value of $\chi^2$ for a respective channel; and
    setting the plurality of parameters to the optimum values for processing data from other channels of data.

* * * * *